(12) United States Patent
Wang et al.

(10) Patent No.: US 12,214,545 B2
(45) Date of Patent: Feb. 4, 2025

(54) THREE-DIMENSIONAL PRINTING METHOD

(71) Applicant: AGENCY FOR SCIENCE, TECHNOLOGY AND RESEARCH, Singapore (SG)

(72) Inventors: Fuke Wang, Singapore (SG); Fei Wang, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 592 days.

(21) Appl. No.: 17/610,729

(22) PCT Filed: Apr. 30, 2020

(86) PCT No.: PCT/SG2020/050260
§ 371 (c)(1),
(2) Date: Nov. 12, 2021

(87) PCT Pub. No.: WO2020/231329
PCT Pub. Date: Nov. 19, 2020

(65) Prior Publication Data
US 2022/0219385 A1    Jul. 14, 2022

(30) Foreign Application Priority Data

May 15, 2019    (SG) ............................ 10201904398P

(51) Int. Cl.
*B29C 64/124* (2017.01)
*B29K 33/00* (2006.01)
(Continued)

(52) U.S. Cl.
CPC ............ *B29C 64/124* (2017.08); *C08L 33/08* (2013.01); *C08L 33/10* (2013.01); *B29K 2033/08* (2013.01);
(Continued)

(58) Field of Classification Search
CPC ... B29C 64/171; B29C 64/165; B29C 64/153; B29C 64/106; B29C 64/10; B29C 64/124
See application file for complete search history.

(56) References Cited

U.S. PATENT DOCUMENTS

2018/0273657 A1    9/2018   Wang et al.
2020/0198231 A1    6/2020   Dubelman et al.

FOREIGN PATENT DOCUMENTS

JP    2017-106082 A    6/2017
WO   WO-2017/192859 A2   11/2017

OTHER PUBLICATIONS

Search Report and Written Opinion in SG Application No. 11202112482V dated Jul. 4, 2023, 10 pages.
(Continued)

*Primary Examiner* — Stella K Yi
(74) *Attorney, Agent, or Firm* — MARSHALL, GERSTEIN & BORUN LLP

(57) ABSTRACT

A method of three-dimensional printing an object having a varying degree of transmissivity to light along an axis of the object, the method comprising the steps of (a) providing a liquefied polymer resin having a plurality of particles therein, the particles being distributed in the liquefied polymer resin based on the density of the particles; and (b) polymerizing the liquefied polymer resin under conditions to form the object layer-by-layer. There is also provided a formulation for three-dimensional printing and a three-dimensional printed object.

17 Claims, 3 Drawing Sheets

(51) Int. Cl.
  *B29L 31/00*  (2006.01)
  *B33Y 10/00*  (2015.01)
  *B33Y 70/10*  (2020.01)
  *B33Y 80/00*  (2015.01)
  *C08L 33/08*  (2006.01)
  *C08L 33/10*  (2006.01)

(52) U.S. Cl.
  CPC ....... *B29L 2031/7536* (2013.01); *B33Y 10/00* (2014.12); *B33Y 70/10* (2020.01); *B33Y 80/00* (2014.12)

(56) References Cited

OTHER PUBLICATIONS

First Office Action in CN Application No. 202080048173.4 dated Mar. 28, 2024, 30 pages.
Search Report in International Application No. PCT/SG2020/050260 dated Oct. 15, 2020, 4 pages.
International Preliminary Report on Patentability in International Application No. PCT/SG2020/050260 dated Jul. 29, 2021, 32 pages.

[Fig. 1]
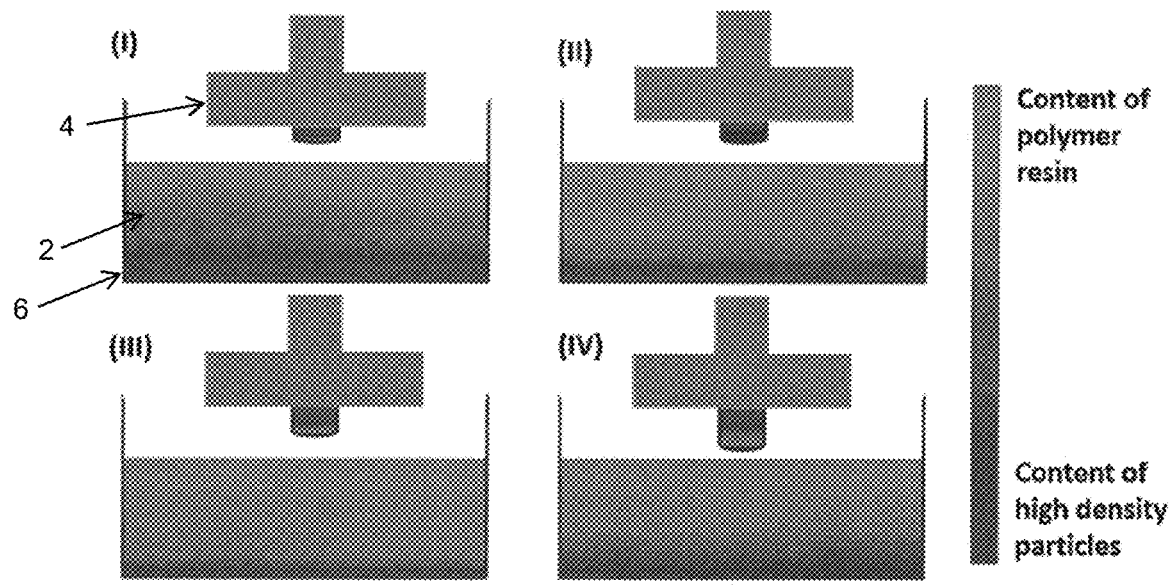
[Fig. 2]
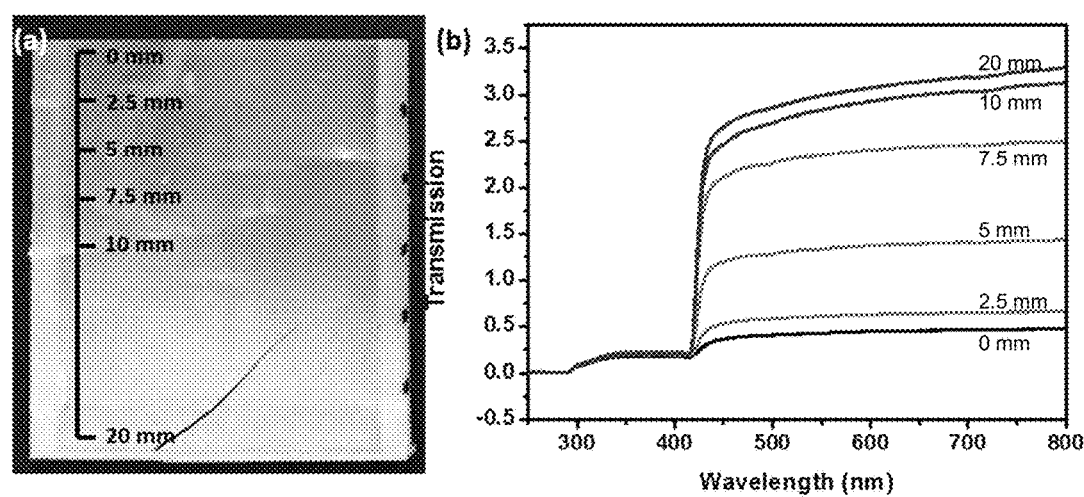

[Fig. 3]
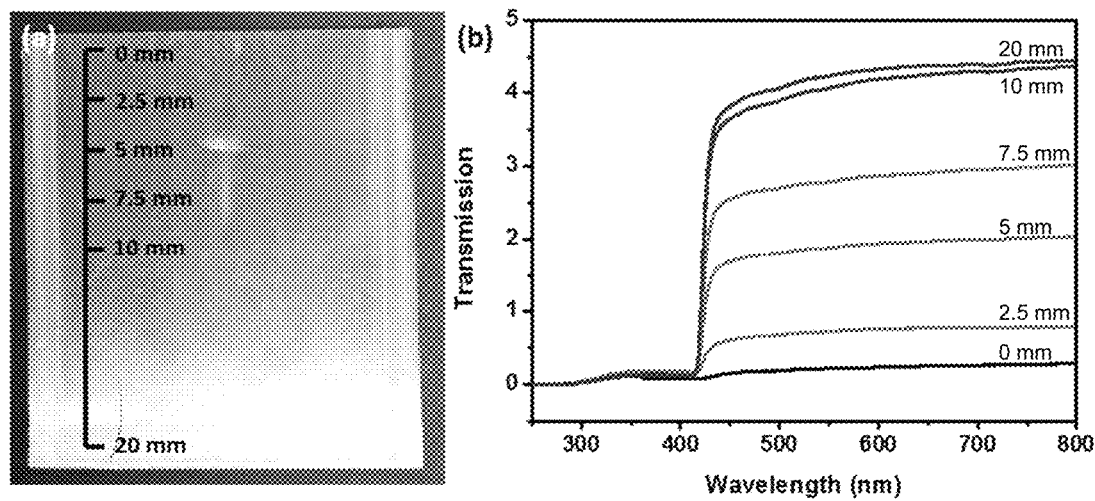
[Fig. 4]
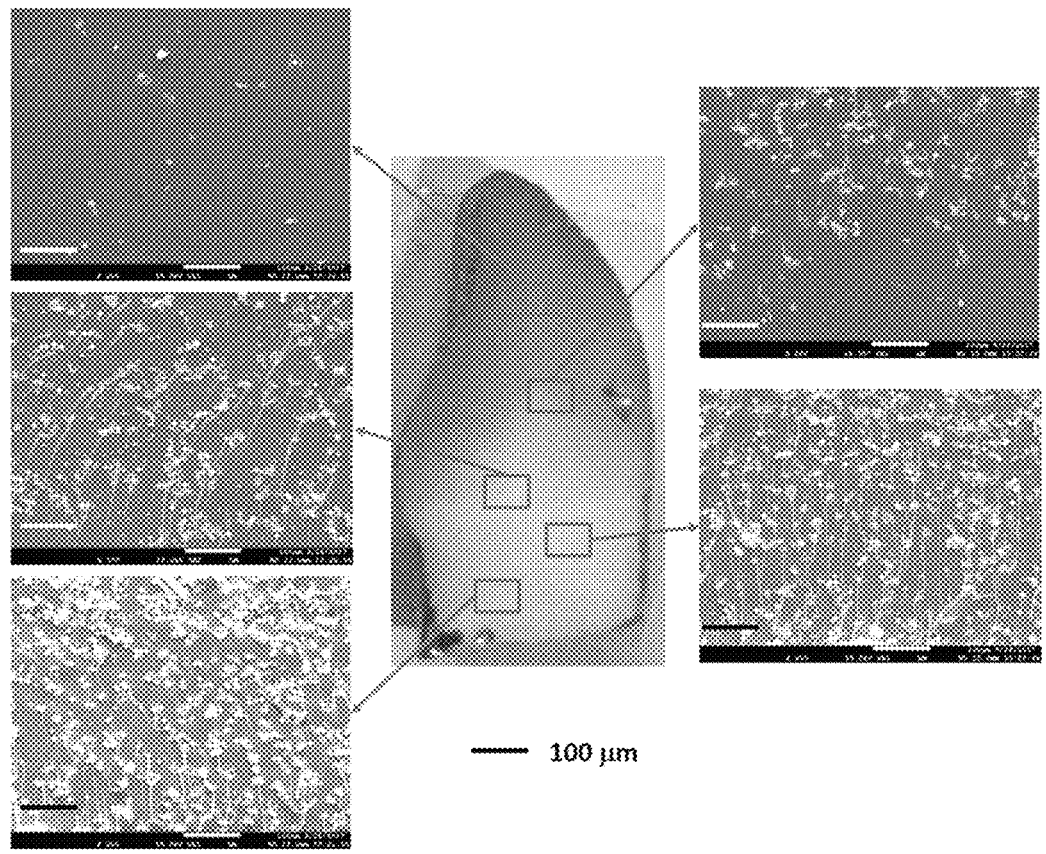

[Fig. 5]
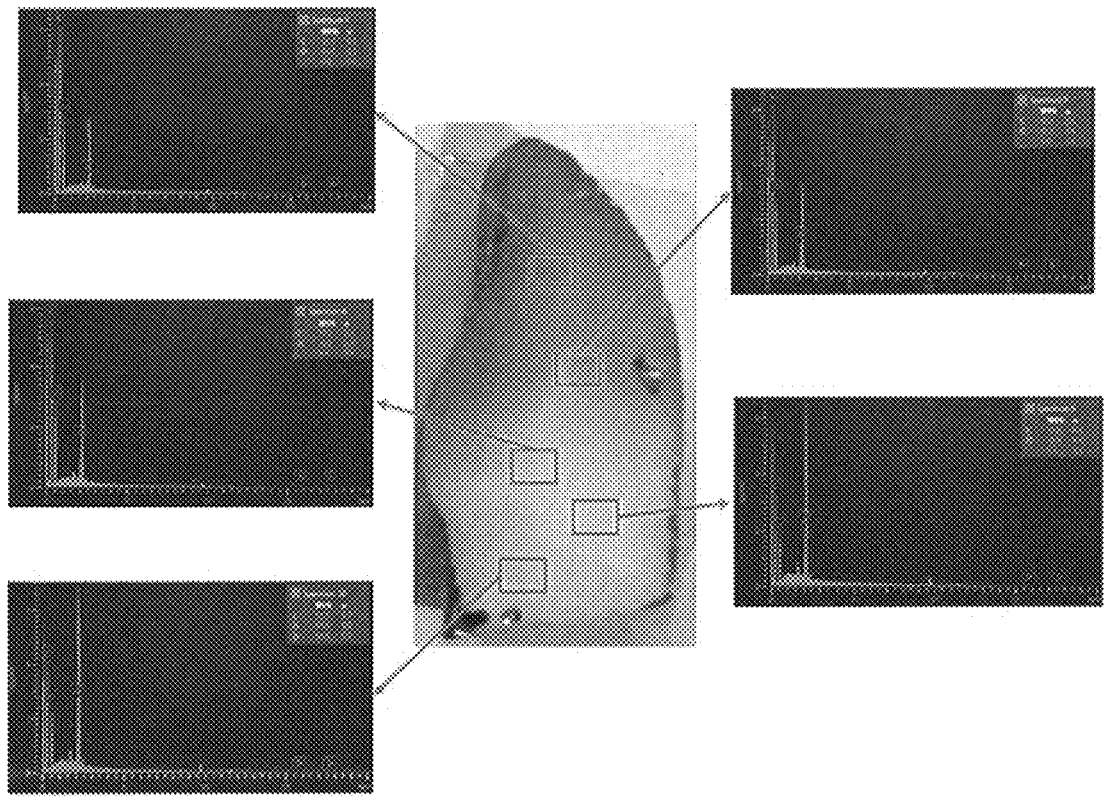
[Fig. 6]
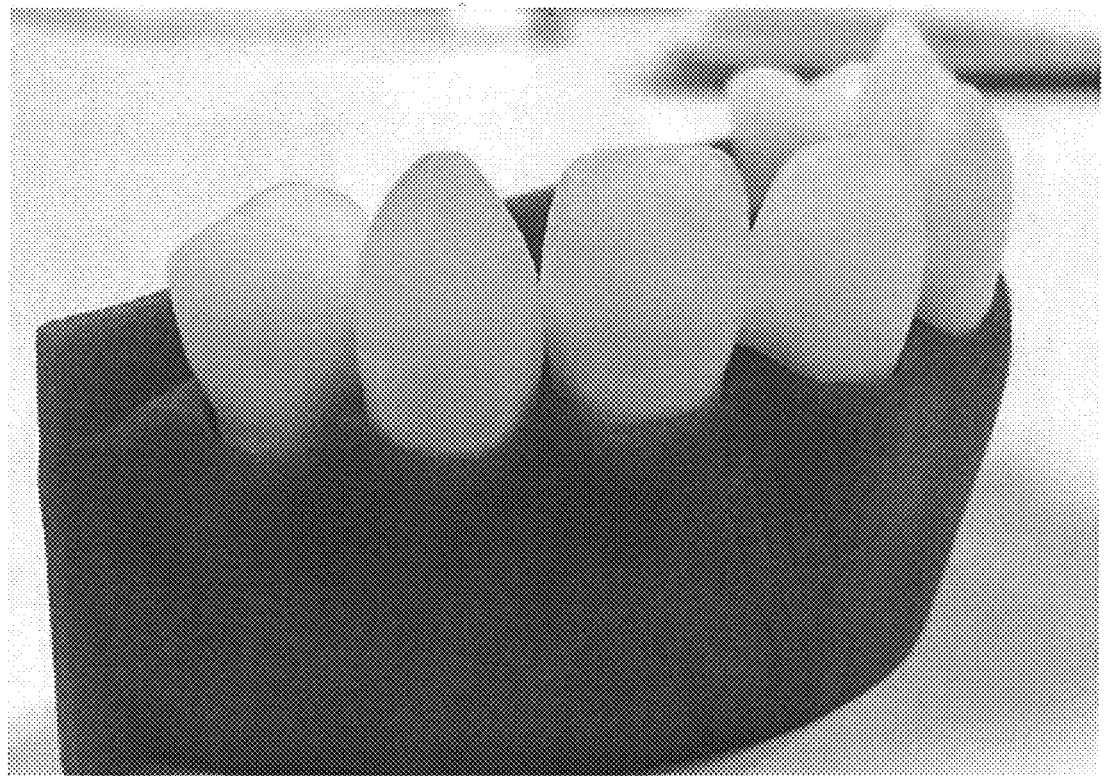

THREE-DIMENSIONAL PRINTING METHOD

TECHNICAL FIELD

The present invention generally relates to method of three-dimensional printing an object. The present invention also relates to a formulation for three-dimensional printing and a three-dimensional printed object.

BACKGROUND ART

The dental industry is one of the strongest motivator for development of new additive manufacturing technologies including new three-dimensional (3D) printers and printable materials. Revenues from dental 3D printing have grown almost 12 percent since 2015. Currently, dental 3D printing is extensively used for making dental implants, dentures, crowns and bridges, etc. The global dental 3D printing market is expected to be worth US$3,427.1 million by the end of 2025. Dental 3D printing market can be divided into three main segments such as metal, polymer resin, ceramic. Polymer resin accounts for largest market for dental 3D printing with a market share of 58.0% in 2016 due to advent in new technology for development of cost effective polymeric material.

Clinical dentistry in general is concerned with aesthetics (about 50%) and the remaining involves materials, mechanical properties, and others. Aesthetic dentistry has become more and more important in the last several decades. The ability to control the colour or match the shade of an artificial tooth to the natural tooth colour of the patient is absolutely important for future dental industry. When an artificial tooth is printed, it is very important to preserve aesthetics by producing it to have a color as similar as possible to the natural tooth. In traditional dental treatment, shade guides have been widely used to match the artificial tooth with natural tooth for a better shade match. However, conventional composite materials are generally monochrome. For natural teeth, the tooth color from the neck to the incisal teeth is gradual, forming a gradient in the colour/shade in the tooth. This is because the chroma of a natural tooth comes mainly from the dentin, and the thickness and opacity of the overlying enamel determines how much chromatic influence the dentin has.

Although attempts to form artificial teeth with gradient color to best match that of natural teeth have been reported, the development of dental printing with gradient color change has not been reported.

Two main type gradient structures have been proposed for the gradient composites, the first being a continuous structure and the second being a stepwise structure. For the continuous gradient structure, the change in composition and microstructures occurs continuously with position. On the other hand, for the stepwise gradient structure, microstructure features changes in a stepwise manner. Classified by the type of gradients, the gradient composites materials can also be divided into the chemical composition gradient materials, the porosity gradient materials, and the microstructural gradient materials.

The manufacturing process of a gradient material can be divided into techniques for gradient film coatings and for bulk gradient materials. Techniques to fabricate gradient thin film include the physical vapour deposition process, the chemical vapour deposition process, and the self-propagating high-temperature synthesis (SHS) process, or a combination of some of these processes. The technologies used to produce the bulk gradient materials include the powder metallurgy method, the centrifugal casting method, the slip casting method, and the tape casting method.

Where powder metallurgy method is used, powder materials are first mixed together, followed by processing of the powder, the forming operations, and the sintering or pressure-assisted hot consolidation. Although the powder metallurgy process is cheaper than other technique, this process produces materials with limited strength and highly intricate parts cannot be produced by this process, which is also complicated to use.

Recently, with the development of the additive manufacturing techniques, many additive manufacturing techniques have been attempted to develop the gradient materials printing. However, till now, only four classes of the additive manufacturing technologies such as Material Extrusion, Powder-Bed Fusion, Directed-Energy Deposition, and sheet lamination have been successfully used for the fabrication of parts of gradient materials.

It has been reported in the literature to fabricate gradient materials using Fused deposition modelling (FDM) and Freeze-form Extrusion Fabrication (FEF) techniques. In a FDM process, the FDM process parameters were mapped with the material properties for the given Acrylonitrile Butadiene Styrene material produced, and then used to develop the gradient materials samples. This showed the possibility of developing gradient materials by FDM technique using different loading conditions. FEF was also used for the fabrication of functionally graded parts using a triple-extruder mechanism, each containing a paste of material. It used a static mixer to blend the different material pastes into a homogeneous paste. The advantages of the material-extrusion process are cost-saving and readily availability. The main disadvantage is that the part quality is limited by the nozzle radius, poor accuracy when compared to the other printing techniques, and the slow processes.

The powder-bed fusion (PBF) process is a class of additive manufacturing technique, where the powdered material (metal, polymer, ceramic) is spread on the building platform and sintered with laser beam or electron beam to form a two-dimensional layer from the sliced 3D CAD file. Numerous additive manufacturing techniques such as selective-laser sintering (SLS), selective laser melting (SLM), selective-heat sintering (SHS), and electron-beam melting (EBM) belong to the PBF class. The main disadvantage of using the PBF technique is the need for vacuum in an inert environment and high temperatures.

Directed-Energy Deposition (DED) is a class of additive manufacturing process that is used to produce 3D objects from a 3D CAD model using energy (such as laser, electron beam, or plasma arc) to create a melt pool on the substrate. The laser-metal deposition process (UM) is a typical DED technique, which is widely used for the repair of high valued components. Laser-direct metal deposition (LDMD) process had been used to form thin-wall gradient structures of Steel 316L and Inconel 718. The results showed that continuously graded materials could be produced using the LDMD process; and that the properties of the functionally graded materials produced can be controlled by controlling the processing parameters.

The sheet-lamination class of the additive manufacturing process includes ultrasonic additive manufacturing (UAM) and laminated object manufacturing (LOM). The successfully fabrication of gradient materials using the sheet-lamination technique was reported by using the ultrasonic consolidation process. Three sheet materials include stainless steel, aluminium, and Copper foils were used in this study and the formation of the gradient structure was demonstrated. The main disadvantages of the lamination techniques is that the finishes achievable depend seriously on the material used and a long post-processing is required to achieve the desired surface finish.

Although above four techniques have been successfully demonstrated to fabricate functionally gradient materials, they suffer from their own disadvantages and have not been used in dental printing with gradient color change.

There is a need to provide a 3D printing method for functionally graded materials that overcomes, or at least ameliorates, one or more of the disadvantages described above.

SUMMARY OF INVENTION

According to a first aspect, there is provided a method of three-dimensional printing an object having a varying degree of transmissivity to light along an axis of the object, the method comprising the steps of (a) providing a liquefied polymer resin having a plurality of particles therein, the particles being distributed in the liquefied polymer resin based on the density of the particles; and (b) polymerizing the liquefied polymer resin under conditions to form the object layer-by-layer.

The method may involve the Vat photopolymerization technique. Vat photopolymerization based printing techniques include laser-based stereolithography (SLA) and digital light processing (DLP) 3D printing. Both techniques can provide high printing resolutions and high surface smoothness, making them ideal techniques for bio-related printing such as dental and bone 3D printing.

Advantageously, the method can be used to print artificial teeth with naturally gradient color change. Therefore, the method provides a 3D printing solution to solve the problem of single color dental prosthesis composite whereby the method can be used to produce a functionally graded artificial tooth with colour gradient from the base of the tooth to the top of the tooth. This enables artificial teeth to be similar in colour and shade as compared to natural teeth.

According to a second aspect, there is provided a three-dimensional printed object having a varying degree of transmissivity to light along an axis of the object.

Definitions

The following words and terms used herein shall have the meaning indicated:

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means+/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and sub-generic groupings falling within the generic disclosure also form part of the disclosure. This includes the generic description of the embodiments with a proviso or negative limitation removing any subject matter from the genus, regardless of whether or not the excised material is specifically recited herein.

DETAILED DISCLOSURE OF EMBODIMENTS

Exemplary, non-limiting embodiments of a method of three-dimensional printing an object will now be disclosed.

The method may comprise the steps of (a) providing a liquefied polymer resin having a plurality of particles therein, the particles being distributed in the liquefied polymer resin based on the density of the particles; and (b) polymerizing the liquefied polymer resin under conditions to form the object layer-by-layer.

The object may be one that has a varying degree of transmissivity to light along an axis of the object. The axis may be along the direction of the three-dimensional printing whereby the zero position of this axis is the place where the first layer starts to be printed and moving positively along the direction where the object is subject to further printing. This axis may be deemed as the "z-axis" and is thereby orthogonal to the x-y plane (whereby the x-y plane is typically the substrate or support where the three-dimensional object is being printed thereon or which forms the base for the layer-by-layer printing of the three-dimensional object). Accordingly, the object may be one that has a varying degree of transmissivity to light along its z-axis.

The varying degree of transmissivity to light may be one whereby the lowest transmissivity to light occurs at the bottom of the object (that is, the zero position of the axis mentioned above) while the greatest transmissivity occurs at the top of the object, away from the zero position of the axis mentioned above (or at the highest possible positive value of the axis mentioned above). The part of the object having the lowest transmissivity to light is deemed as being opaque or partially opaque to the passage of light through the object while the part of the object having the greatest transmissivity to light does not mean that this part of the object is completely transparent but that this part of the object allows more light to pass through (and is therefore less opaque or in the alternative, more translucent) than the part of the object having the lowest transmissivity to light. Along the axis mentioned above, the lowest transmissivity to light occurs at the zero position of the axis and increases along the axis such that the greatest transmissivity occurs at the highest possible positive value on the axis. The varying degree of transmissivity may be one which changes along the axis in a random manner (that is, the transmissivity may be higher or lower than another point along the axis as long as the greatest transmissivity occurs at the highest possible positive value of the axis). The varying degree of transmissivity may be one which gradually increases along the axis such that a point on the object having a higher positive value on the axis would always have a greater transmissivity than a point having a lower positive value on the axis.

It is to be appreciated that the above can also be viewed in the reverse, that is, the varying degree of transmissivity to light may be one whereby the lowest transmissivity to light occurs at the top of the object (that is, the highest possible positive value of the axis mentioned above) while the greatest transmissivity occurs at the bottom of the object (that is at the zero position of the axis mentioned above). Therefore, the greatest transmissivity to light occurs at the zero position of the axis and decreases along the axis such that the lowest transmissivity occurs at the highest possible positive value on the axis.

The varying degree of transmissivity along the object may present as a colour change or colour gradient that can be observed when viewing the external surface of the object. The colour could be regarded as being more "dense" or having a deeper shade at the point of the object having a lower transmissivity and being "lighter" or having a lighter shade at the point of the object having a greater transmissivity.

The transmissivity to light may be regarded as being visible light, which has a wavelength in the range of about 380 to about 740 nanometers.

The method may further comprise, before the providing step (a), the steps of (a1) providing a homogenous suspension of the particles within the liquefied polymer resin; and (a2) allowing the particles to distribute within the liquefied polymer resin based on their density values after a period of time. The particles may be mixed within the liquefied polymer resin for a period of time. The particles may be mixed by subjecting the mixture to a shearing force, a mixing force or ultrasonication mixing. The mixing may be undertaken for a period of at least 1 hour, at least 2 hours, at least 3 hours, or at least 4 hours. The liquefied polymer resin may then be allowed to stand for a period of time in the range of a few minutes to one hour, or about 5 minutes to 30 minutes, to allow sedimentation to occur whereby the particles within the liquefied polymer resin separate based on difference in density, resin viscosity, particle sizes and/or particle shape under the influence of gravity. Due to the use of different types of particles that have different density values or use of the same kind of particles (that is, particles of the same material) but having different shapes/sizes leading to different density values, the particles with the same density values will settle in the same region of the liquefied polymer resin such that there is a variation in the types of particles when moving from the bottom of the liquefied polymer resin to the top of the liquefied polymer resin. The particles with the greatest or greater density values will settle at the bottom of the liquefied polymer resin while those with smaller density values will settle at the regions above, leading to a distribution of the particles within the liquefied polymer resin based on the density of the particles. Due to this distribution of particles within the liquefied polymer resin, this will determine the light transmissivity of the final printed object since parts of the printed object having more particles therein will have a lower transmissivity to light while parts of the printed object having less particles therein will have a greater transmissivity to light. The particles may be coloured and therefore contribute to the colour change or colour gradient along the object.

The liquefied polymer resin may further comprise a photoinitiator and optionally a photoadditive selected from a photoabsorber or a photostabilizer. The photoinitiator and the optional photoadditive may be added to the liquefied polymer resin containing particles and mixed to form a homogeneous suspension. In order to avoid premature polymerization of the polymer resin, the mixing is conducted in the absence of light. The mixture may be stirred using any suitable mixing technique for a suitable period of time. For example, where the mixing technique used is magnetic stirring, mechanical stirring or shaking, the mixing time can be about 8 hours to about 24 hours, about 8 hours to about 12 hours, about 8 hours to about 18 hours, about 12 hours to about 24 hours, or about 18 hours to about 24 hours to form the homogeneous suspension. When the mixing technique is homogenization and/or ultrasonication, the mixing time can be about 10 minutes to about 15 minutes, about 10 minutes to about 30 minutes, about 10 minutes to about 45 minutes, about 10 minutes to about 60 minutes, about 10 minutes to about 75 minutes, about 10 minutes to about 90 minutes, about 10 minutes to about 105 minutes, about 15 minutes to about 2 hours, about 30 minutes to about 2 hours, about 45 minutes to about 2 hours, about 60 minutes to about 2 hours, about 75 minutes to about 2 hours, about 90 minutes to about 2 hours, or about 105 minutes to about 2 hours.

The liquefied polymer resin may have a viscosity in the range of about 100 to about 1000 cps, about 100 to about 900 cps, about 100 to about 800 cps, about 100 to about 700 cps, about 100 to about 600 cps, about 100 to about 500 cps, about 100 to about 400 cps, about 100 to about 300 cps, about 100 to about 200 cps, about 200 to about 1000 cps, about 300 to about 1000 cps, about 400 to about 1000 cps, about 500 to about 1000 cps, about 600 to about 1000 cps, about 700 to about 1000 cps, about 800 to about 1000 cps, or about 900 to about 1000 cps. Depending on the viscosity of the resin, this will affect the light transmissivity in the formed object and therefore affect the optical effect of the formed object. In general, the liquefied polymer resin may have a uniform viscosity, which will affect the dispersion of the particles. If particles having a large density are used, then liquefied polymer resins with a large viscosity will be chosen for use. Similarly, if particles having a low density are used, then liquefied polymer resins with a low density will be chosen for use.

The liquefied polymer resin may then be subjected to polymerization to form the object layer-by-layer. This may involve the use of vat photopolymerization where the liquefied polymer resin is placed in a vat and a support arm is moved within the vat to allow exposure of a thin layer of the liquefied polymer resin to a light source near the surface of the liquefied polymer resin in order to initiate polymerization of that layer. Once one layer is polymerized, the support arm then moves to again expose another thin layer of the liquefied polymer resin to the light source to polymerize a subsequent layer. This is repeated until the object is formed. The light source may be ultraviolet light, a laser or any suitable light source that is able to excite the photoinitiator present in the liquefied polymer resin to start the polymerization process.

The formed object may be subjected to post-treatment such as washing, drying and further curing. Therefore, the formed object may be washing using an organic solvent (such as iso-propanol) to remove any excess liquefied polymer resin and then dried. In order to complete the curing process, the formed object may be placed in an ultraviolet oven.

The method may be used with any conventional three-dimensional printer with any conventional three-dimensional printing software.

Exemplary, non-limiting embodiments of a formulation for three-dimensional printing will now be disclosed.

The formulation for three-dimensional printing comprises
(i) a liquefied polymer resin;
(ii) a plurality of particles having various density values;
(iii) a photoinitiator; and
(iv) optionally a photoadditive.

The various components may be present in the formulation based on the following:
(i) 60 to 95 wt % liquefied polymer resin;
(ii) 0.5 to 40 wt % particles;
(iii) 0.1 to 5 wt % photoinitiator; and
(iv) 0 to 0.2 wt % photoadditive,
based on the weight of the formulation.

The liquefied polymer resin may comprise an acrylate. It is to be appreciated that any acrylate that is suitable for three-dimensional printing can be used here. Exemplarily, the acrylate may be a monomer or oligomer selected from the group consisting of bisphenol A dimethacrylate (Bis-DMA), bisphenol A diglycidyl ether methacrylate (Bis-GMA), ethoxylated bisphenol-A dimethacrylate (Bis-EMA), Tricyclo[5.2.1.02,6]decanedimethanol diacrylate, Bisphenol A glycerolate diacrylate, Bisphenol A ethoxylate diacrylate, Bisphenol A ethoxylate dimethacrylate (oligo), Bisphenol F ethoxylate diacrylate (oligo), Poly(ethylene glycol) diacrylate, Di(ethylene glycol) diacrylate, Tetra(ethylene glycol) diacrylate, 1,4-Butanediol diacrylate, Hydroxy ethylmethacrylate, 3,4-epoxy-cyclohexyl-methyl methacrylate (METHB), triethylene glycol dimethacrylate (TEGDMA), Tertiobutyl cyclohexanol methacrylate, 1,6-bis[2-(methacryloyloxy) ethoxycarbonylamino]-2,4,4-trimethylhexane (UDMA), 3,3,5-trimethyl cyclohexanol methacrylate, Dipentaerythritol penta-/hexa-acrylate and mixtures thereof.

The particles in the formulation may have densities in the range of about 3.00 g/cm3 to about 12.00 g/cm$^3$, about 3.00 g/cm$^3$ to about 4.00 g/cm$^3$, about 3.00 g/cm$^3$ to about 5.00 g/cm$^3$, about 3.00 g/cm$^3$ to about 6.00 g/cm$^3$, about 3.00 g/cm$^3$ to about 7.00 g/cm$^3$, about 3.00 g/cm$^3$ to about 8.00 g/cm$^3$, about 3.00 g/cm$^3$ to about 9.00 g/cm$^3$, about 3.00 g/cm$^3$ to about 10.00 g/cm$^3$, about 3.00 g/cm$^3$ to about 11.00 g/cm$^3$, about 4.00 g/cm$^3$ to about 12.00 g/cm$^3$, about 5.00 g/cm$^3$ to about 12.00 g/cm$^3$, about 6.00 g/cm$^3$ to about 12.00 g/cm$^3$, about 7.00 g/cm$^3$ to about 12.00 g/cm$^3$, about 8.00 g/cm$^3$ to about 12.00 g/cm$^3$, about 9.00 g/cm$^3$ to about 12.00 g/cm$^3$, about 10.00 g/cm$^3$ to about 12.00 g/cm$^3$, or about 11.00 g/cm$^3$ to about 12.00 g/cm$^3$. As mentioned above, depending on the density value, the particles will settle or distribute within the liquefied polymer resin, forming a gradient of the particles within the liquefied polymer resin based on their density values whereby the particles with higher density values will settle at the bottom of the liquefied polymer resin due to gravity while the particles with smaller density values will be present at regions above the denser particles.

The particles may have a particle size that is in the range of nanometers or micrometers. The particle size may be in the range of about 50 nm to about 50 microns, about 50 nm to about 100 nm, about 50 nm to about 200 nm, about 50 nm to about 500 nm, about 50 nm to about 1 microns, about 50 nm to about 5 microns, about 50 nm to about 10 microns, about 50 nm to about 15 microns, about 50 nm to about 20 microns, about 50 nm to about 25 microns, about 50 nm to about 30 microns, about 50 nm to about 35 microns, about 50 nm to about 40 microns, about 50 nm to about 45 microns, about 100 nm to about 50 microns, about 200 nm to about 50 microns, about 500 nm to about 50 microns, about 1 micron to about 50 microns, about 5 microns to about 50 microns, about 10 microns to about 50 microns, about 15 microns to about 50 microns, about 20 microns to about 50 microns, about 25 microns to about 50 microns, about 30 microns to about 50 microns, about 35 microns to about 50 microns, about 40 microns to about 50 microns, or about 45 microns to about 50 microns.

The particles may have a shape that is not particularly limited and may be spheres, rods, fibers, plates or star-shaped.

The particles that may be used in the method may not be particularly limited as long as they have a density value in the range above. Exemplarily, the particles may be selected from the group consisting of metal oxides, metal nitrides, metal carbides, metalloid oxides, metalloid nitrides and metalloid carbides. The metal or metalloid of the metal oxides, metal nitrides, metal carbides, metalloid oxides, metalloid nitrides or metalloid carbides may be selected from Group 2, Group 3, Group 4, Group 5, Group 6, Group 8, Group 11, Group 12, Group 13, Group 14 or the lanthanide series of the Periodic Table of Elements. The particles may be selected from the group consisting of zinc oxide (5.61 g/cm$^3$), Silicon carbide (3.21 g/cm$^3$), Silicon nitride (3.44 g/cm$^3$), Gallium nitride (6.15 g/cm$^3$), Aluminium oxide (3.95 g/cm$^3$), Titanium dioxide (4.23 g/cm$^3$), Zirconium dioxide (5.68 g/cm$^3$), Tin dioxide (5.61 g/cm$^3$), Iron (III) oxide (5.24 g/cm$^3$), Magnesium oxide (3.58 g/cm$^3$), Indium (III) oxide (7.18 g/cm$^3$), Tungsten trioxide (7.16 g/cm$^3$), Tungsten (IV) oxide (10.8 g/cm$^3$), Silver oxide (7.14 g/cm$^3$), Vanadium (V) oxide (3.36 g/cm$^3$), Vanadium (IV) oxide (4.57 g/cm$^3$), Molybdenum trioxide (4.69 g/cm$^3$), Yttrium (III) oxide (5.01 g/cm$^3$), Cerium (IV) oxide (7.22 g/cm$^3$) and Copper (II) oxide (6.31 g/cm$^3$). A mixture of different types of particles having different density values can be used or the same type of particles (that is, all of the particles are from the same material) can be used but having varying shapes/sizes in order to create a plurality of particles having different density values.

The photoinitiator used in the formulation may not be particularly limited and may be dependent on the type of acrylate used. The photoinitiator may be a type I or type II photoinitiator. Exemplarily, the photoinitiator may be selected from the group consisting of bis(2,4,6-trimethyl benzoyl)phenylphosphine oxide (IRGACURE 819), Phenyl-bis(2,4,6-trimethylbenzoyl)phosphine oxide (BAPO), 2,4,6-trimethylbenzoyl diphenyl phosphine (TPO), 2-hydroxy-2-methyl-1-phenyl-1-propane (DAROCUR 1173) and benzophenone (BP).

The photoadditive used in the formulation may not be particularly limited and may be a photoabsorber. Exemplarily photoabsorber may be selected from the group consisting of Sudan I-IV, 2,5-Bis(5-tert-butyl-benzoxazol-2-yl)thiophene, 4-methoxyphenol and butylated hyrdorxytoluene.

Exemplary, non-limiting embodiments of a three-dimensional printed object will now be disclosed.

The three-dimensional printed object may have a varying degree of transmissivity to light along an axis of the object. The varying degree of transmissivity to light may be along the z-axis of the object.

The three-dimensional printed object may be regarded as having a functional gradient in the colour along the axis. The three-dimensional printed object may be a tooth or an implant for use in a human or animal body. Where the three-dimensional printed object is to be used as an surgical or biological object, it is to be noted that the components of the formulation to form the three-dimensional printed object may not be toxic or harmful to the host.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

FIG. 1 is a schematic diagram showing an embodiment of the disclosed three-dimensional printing method.

FIG. 2a is a photo of a side view of a printed plate made in accordance to Example 1 below. [FIG. 2b] is a graph showing the transparency change as a function of the position of the printed plate.

FIG. 3a is a photo of a side view of a printed plate made in accordance to Example 2 below. [FIG. 3b] is a graph showing the transparency change as a function of the position of the printed plate.

FIG. 4 is an image showing the cross-section of a printed tooth made in accordance to Example 3 below.

FIG. 5 is an image showing the cross-section of a printed tooth made in accordance to Example 3 below.

FIG. 6 is a photograph showing a number of prototypes of the artificial teeth made in accordance with Example 4 below.

DETAILED DESCRIPTION OF DRAWINGS

Referring to FIG. 1, there is provided a schematic diagram showing an embodiment of the disclosed three-dimensional printing method which is based on digital light processing. In FIG. 1(I), a liquefied polymer resin 2 is first provided in a vat 6. The liquefied polymer resin 2 is as described above. When the liquefied polymer resin 2 is left to settle under the influence of gravity, sedimentation potential occurs. The high density particles present in the liquefied polymer resin 2 are suspended or sediment at rates that depend on the following factors: difference in density, fluid viscosity, particle sizes and particle shape. Therefore, when high density particles are blended with Vat polymers for the liquid resin based three-dimensional printing, the high density particles will form a sedimentation gradient in the tank under the influence of gravity (FIG. 1(I)). When the platform 4 is lowered down to print, the solidified materials at the starting layers will have higher content particles due to particles sedimentation. With continue printing processing, more and more particles are solidified into the polymers resin, and the concentration of particles in the liquid polymer resin will drop correspondingly. As shown in FIG. 1, the particles concentration is continually decreased with the printing process (moving from FIG. 1(I), to FIG. 1(II), to FIG. 1(III) to FIG. 1(IV)), and finally there are limited particles left in the resin and thus a more and more transparent solid is formed. In this way, the printed structures will show a gradient color change from the bottom to top, and also the transparency will show a similar gradient change. With this method, it is possible to produce one dimensional gradient of component materials content in the printed structure. Due to sedimentation process, the highest filler content is expected in the lowest printed layer.

EXAMPLES

Non-limiting examples of the invention be further described in greater detail by reference to specific Examples, which should not be construed as in any way limiting the scope of the invention.

Example 1

Resin Formulation

The base resin and the particles (all chemicals from Aldrich Sigma of St. Louis of Missouri of the United States of America) (Table 1) were weighed into a flask and ultra-sonicated in an ultrasonic bath for at least 2 hours. Then the photoinitiators and photostabilizer were added into the mixture and stirred in the absence of light for 8 to 24 hrs until a homogeneous suspension was obtained.

TABLE 1 formulation of resin 1

| Ingredient | Percentages (wt %) |
| --- | --- |
| Bisphenol A ethoxylate diacrylate (average Mn ~468) | 35 |
| Di(ethylene glycol) dimethacrylate (Aldrich) | 60 |
| zinc oxide (particles sizes <5 μm) | 4.4 |
| Phenylbis(2,4,6-trimethylbenzoyl)phosphine oxide | 0.5 |
| 4-methoxyphenol | 0.1 |

Printing of the Structures with Gradient Optical Properties Change

To demonstrate the possibility of gradient color printing, a rectangle plate was printed on a DLP printer (LittleRP with build volume 60 mm (X) 40 mm (Y) 100 mm (Z), which uses dynamic light processing projector with a resolution of 1024×768 (Brand & model: Acer P128) as light source and Creation Workshop as controlling software.) Printing was carried out with slice thickness of 50 μm. Exposure time per layer was 6 seconds. After printing, the printed part was washed thoroughly with iso-propanol, air dried and placed inside UV oven for further curing. The printed structure with gradient colour change is shown in FIG. 2a. In addition, the gradient change in transparency was evaluated by using UV-vis spectrometer. The difference in transparency was measured at different position and the results were plotted in FIG. 2b.

Example 2

Resin Formulation

The base resin and the particles (Table 2) were weighed into a flask and ultrasonicated in an ultrasonic bath for at least 2 hours. Then the photoinitiators and photostabilizer were added into the mixture and stirred in the absence of light for 8 to 24 hrs until a homogeneous suspension was obtained.

TABLE 2 formulation of resin 2

| Ingredient | Percentages (wt %) |
| --- | --- |
| Bisphenol A ethoxylate diacrylate (average Mn ~468) | 23 |
| Di(ethylene glycol) dimethacrylate | 70 |
| Zirconium dioxide (325 mesh) | 6.4 |
| Phenylbis(2,4,6-trimethylbenzoyl)phosphine oxide | 0.5 |
| 4-methoxyphenol | 0.1 |

Printing of the Structures with Gradient Optical Properties Change

To demonstrate the possibility of gradient color printing, a rectangle plate was printed on a DLP printer (LittleRP with build volume 60 mm (X) 40 mm (Y) 100 mm (Z), which uses dynamic light processing projector with a resolution of 1024×768 (Brand & model: Acer P128) as light source and Creation Workshop as controlling software.) Printing was carried out with slice thickness of 50 µm. Exposure time per layer was 6 seconds. After printing, the printed part was washed thoroughly with iso-propanol, air dried and placed inside UV oven for further curing. The printed structure with gradient colour change is shown in FIG. 3a. In addition, the gradient change in transparency was evaluated by using UV-vis spectrometer. The difference in transparency was measured at different position and the results were plotted in FIG. 3b.

Example 3—Dental Printing and Characterization

Resin Formulation

The base resin and the particles (Table 3) were weighed into a flask and ultrasonicated in an ultrasonic bath for at least 2 hours. Then the photoinitiators and photstabilizer were added into the mixture and stirred in the absence of light for 8 to 24 hrs until a homogeneous suspension was obtained.

TABLE 3 formulation of resin 3

| Ingredient | Percentages (wt %) |
| --- | --- |
| Bisphenol A ethoxylate diacrylate (average Mn ~468) | 31 |
| Di(ethylene glycol) dimethacrylate | 60 |
| Zirconium dioxide (325 mesh) | 8.4 |
| Phenylbis(2,4,6-trimethylbenzoyl)phosphine oxide | 0.5 |
| 2,5-Bis(5-tert-butyl-benzoxazol-2-yl)thiophene | 0.1 |

Printing of the Structures with Gradient Optical Properties Change

To demonstrate the possibility the artificial tooth with gradient color change, the tooth structure was printed on a DLP printer (LittleRP with build volume 60 mm (X) 40 mm (Y) 100 mm (Z), which uses dynamic light processing projector with a resolution of 1024×768 (Brand & model: Acer P128) as light source and Creation Workshop as controlling software.) Printing was carried out with slice thickness of 50 µm. Exposure time per layer was 6 seconds. After printing, the printed part was washed thoroughly with iso-propanol, air dried and placed inside UV oven for further curing. The printed structure was cut and the cross section cutting image is shown in FIG. 4 and FIG. 5. The cut structure was measured by scanning electron microscopy to identify both the particle distribution (FIG. 4) and the gradient change structure was also confirmed by energy-dispersive X-ray spectroscopy measurement (FIG. 5).

Referring to FIG. 4, the peripheral photos show that the concentration of the pigments (white particles in the photo) increased in the cross-section of the printed tooth from top to bottom (the sequence of the photos from top to bottom is: left top, right top, left middle, right bottom and left bottom). Therefore, the greatest concentration of the pigments was at the bottom of the printed tooth while the lowest concentration of the pigments was at the top of the printed tooth.

Referring to FIG. 5, the peripheral photos show that the elemental abundance of pigments increased in the cross-section of the printed tooth from top to bottom (the sequence of the photos from top to bottom is: left top, right top, left middle, right bottom and left bottom). Similar to FIG. 4, the greatest abundance of the pigments was at the bottom of the printed tooth while the lowest abundance of the pigments was at the top of the printed tooth.

Example 4—Prototype Printing

To demonstrate the application of the present technique in dental printing, a set of teeth with gradient color change was printed on a DLP printer (LittleRP with build volume 60 mm (X) 40 mm (Y) 100 mm (Z), which uses dynamic light processing projector with a resolution of 1024×768 (Brand & model: Acer P128) as light source and Creation Workshop as controlling software.) The resin used is the same as described in Example 3. Printing was carried out with slice thickness of 50 µm. Exposure time per layer was 6 seconds. After printing, the printed part was washed thoroughly with iso-propanol, air dried and placed inside UV oven for further curing. The printed prototype was displayed in FIG. 6, which shows clearly the gradient colour change of the printed teeth.

INDUSTRIAL APPLICABILITY

The disclosed method can be used to three-dimensional print an object having a varying degree of transmissivity to light along an axis of the object. The three-dimensional printed object may be used as an artificial tooth whereby the artificial tooth has more opacity in the cervical area and more translucency in the incisal area.

The three-dimensional printed object may be used as an implant in a human or animal body, such as an artificial bone. The three-dimensional printed object may be used to form artificial materials that mimic those found in nature that are functionally graded, such as wood or bamboo.

The disclosed method may be used in engineering devices development whereby the materials formed may have graded combinations of flexibility, elasticity or rigidity.

The disclosed method may be used in fire retardant applications such as forming spacecraft heat shields or heat exchanger tubes.

The disclosed method may be used in electronics or optoelectronics such as in optical fibers for high speed transmission.

The disclosed method may be used in defense such as in armour plates or bullet-proof vests.

The disclosed method may be used in thermal barrier coatings such as in automotive, aircraft industries and power plant to reduce heat loss from engine exhaust systems.

The disclosed method may be used in energy applications such as in energy conversion devices.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. A method of three-dimensional printing an object having a varying degree of transmissivity to light along an axis of said object, the method comprising the steps of:
   (a) providing a liquefied polymer resin having a plurality of particles therein, wherein said particles have densities in a range of 3 g/cm$^3$ to 12 g/cm$^3$, said particles being distributed in said liquefied polymer resin based on the density of said particles; and
   (b) polymerizing said liquefied polymer resin to form said object layer-by-layer by exposing each layer to light.

2. The method according to claim 1, further comprising, before said providing step (a), the steps of:
   (a1) providing a homogenous suspension of said particles within said liquefied polymer resin; and
   (a2) allowing the particles to distribute within said liquefied polymer resin based on their density values after a period of time.

3. The method according to claim 1, wherein said liquefied polymer resin further comprises a photoinitiator.

4. The method according to claim 1, wherein said liquefied polymer resin further comprises a photoadditive selected from a photoabsorber or a photostabilizer.

5. The method according to claim 1, further comprising the step of: (c) post-treating the formed object.

6. A formulation for three-dimensional printing comprising:
   (i) 60 wt % to 95 wt % liquefied polymer resin;
   (ii) 5 wt % to 40 wt % particles;
   (iii) 0.1 wt % to 5 wt % photoinitiator; and
   (iv) 0 to 0.2 wt % photoadditive, based on the weight of the formulation;
   wherein said particles comprise a plurality of particles having various density values; and
   wherein said particles have densities in a range of 3 g/cm$^3$ to 12 g/cm$^3$.

7. The formulation according to claim 6, wherein said particles have a particle size in a range of 50 nm to 50 microns.

8. The formulation according to claim 6, wherein said particles have a shape that is selected from the group consisting of spheres, rods, fibers, plates, and star-shaped.

9. The formulation according to claim 6, wherein said liquefied polymer resin comprises an acrylate.

10. The formulation according to claim 9, wherein said acrylate is a monomer or oligomer selected from the group consisting of bisphenol A dimethacrylate (Bis-DMA), bisphenol A diglycidyl ether methacrylate (Bis-GMA), ethoxylated bisphenol-A dimethacrylate (Bis-EMA), Tricyclo[5.2.1.02,6]decanedimethanol diacrylate, Bisphenol A glycerolate diacrylate, Bisphenol A ethoxylate diacrylate, Bisphenol A ethoxylate dimethacrylate (oligo), Bisphenol F ethoxylate diacrylate (oligo), Poly(ethylene glycol) diacrylate, Di(ethylene glycol) diacrylate, Tetra(ethylene glycol) diacrylate, 1,4-Butanediol diacrylate, Hydroxy ethylmethacrylate, 3,4-epoxy-cyclohexyl-methyl methacrylate (METHB), triethylene glycol dimethacrylate (TEGDMA), Tertiobutyl cyclohexanol methacrylate, 1,6-bis[2-(methacryloyloxy) ethoxycarbonylamino]-2,4,4-trimethylhexane (UDMA), 3,3,5-trimethyl cyclohexanol methacrylate, Dipentaerythritol penta-/hexa-acrylate, and mixtures thereof.

11. The formulation according to claim 6, wherein said particles are selected from the group consisting of metal oxides, metal nitrides, metal carbides, metalloid oxides, metalloid nitrides, and metalloid carbides.

12. The formulation according to claim 11, wherein the metal or metalloid of said metal oxides, metal nitrides, metal carbides, metalloid oxides, metalloid nitrides, or metalloid carbides is selected from the group consisting of Group 2, Group 3, Group 4, Group 5, Group 6, Group 8, Group 11, Group 12, Group 13, Group 14, and the lanthanide series of the Periodic Table of Elements.

13. The formulation according to claim 12, wherein said particles are selected from the group consisting of zinc oxide, Silicon carbide, Silicon nitride, Gallium nitride, Aluminium oxide, Titanium dioxide, Zirconium dioxide, Tin dioxide, Iron (III) oxide, Magnesium oxide, Indium (III) oxide, Tungsten trioxide, Tungsten (IV) oxide, Silver oxide, Vanadium (V) oxide, Vanadium (IV) oxide, Molybdenum trioxide, Yttrium (III) oxide, Cerium (IV) oxide, and Copper (II) oxide.

14. The formulation according to claim 6, wherein said photoinitiator is a type I or type II photoinitiator.

15. The formulation according to claim 14, wherein said photoinitiator is selected from the group consisting of bis (2,4, 6-trimethyl benzoyl)phenylphosphine oxide (IRGACURE 819), Phenylbis(2,4,6-trimethylbenzoyl) phosphine oxide (BAPO), 2,4,6-trimethylbenzoyl diphenyl phosphine (TPO), 2-hydroxy-2-methyl-1-phenyl-1-propane (DAROCUR 1173), and benzophenone (BP).

16. The formulation according to claim 6, wherein said photoadditive is a photoabsorber selected from the group consisting of Sudan I-IV, 2,5-Bis(5-tert-butyl-benzoxazol-2-yl)thiophene, 4-methoxyphenol, and butylated hyrdorxytoluene.

17. A three-dimensional printed object having a varying degree of transmissivity to light along an axis of said object; wherein along said axis, a transparency of said object varies gradationally from opaque or partially opaque on one end to translucent or transparent on an opposite end; and wherein said object is formed from the formulation according to claim 6.

* * * * *